United States Patent [19]

Engelhardt et al.

[11] Patent Number: 4,845,284
[45] Date of Patent: Jul. 4, 1989

[54] SUBSTITUTED 3-NITROBENZENESULFONAMIDES USEFUL AS ADJUNCTS IN RADIATION THERAPY

[75] Inventors: Edward L. Engelhardt, Gwynedd Valley; Walfred S. Saari, Landsdale, both of Pa.

[73] Assignee: Merck & Co., Inc., Rahway, N.J.

[21] Appl. No.: 937,275

[22] Filed: Dec. 3, 1986

[51] Int. Cl.$^4$ ............................................ C07C 143/78
[52] U.S. Cl. ........................................ 564/87; 564/93
[58] Field of Search ................... 564/87, 93; 514/603, 514/605

[56] References Cited

U.S. PATENT DOCUMENTS

| | | | |
|---|---|---|---|
| 2,531,755 | 11/1950 | Waletzky | 514/603 |
| 3,066,158 | 4/1961 | Sayigh | 260/397.7 |
| 4,113,463 | 9/1978 | Oshio et al. | 564/87 |
| 4,603,133 | 7/1986 | Engelhardt et al. | 514/229 |
| 4,665,227 | 5/1987 | Colatsky et al. | 564/87 |

FOREIGN PATENT DOCUMENTS

| | | | |
|---|---|---|---|
| 0138720 | 4/1985 | European Pat. Off. | 564/87 |
| 0138721 | 4/1985 | European Pat. Off. | 564/87 |
| 0197386 | 10/1986 | European Pat. Off. | 564/87 |
| 2332979 | 1/1974 | Fed. Rep. of Germany | 564/87 |
| 205901 | 1/1984 | Fed. Rep. of Germany | 544/159 |
| 2114563 | 8/1983 | United Kingdom | 564/87 |

OTHER PUBLICATIONS

Narayanan, V. L. et al., Development of Radiosensitizers 19:155-205 (1982).
Narayanan, V. L. et al. Development of Radiosensitizers 19, 174-175 (1982).
Halliwell, B. et al., Free Radicals in Biology and Medicine Oxford 1985, pp. 238-241.
Wardman, P. "Radiation Chemistry in the Clinic:-Hypoxic Cell Radiosensitizers for Radiotherapy" manuscript to be published.

Primary Examiner—Robert T. Bond
Assistant Examiner—Raymond Covington
Attorney, Agent, or Firm—Charles M. Caruso; Roy D. Meredith; Hesna J. Pfeiffer

[57] ABSTRACT

This application discloses new substituted 3-nitrobenzensulfonamides which are useful in enhancing the effect of therapeutic radiation. It also discloses pharmaceutical composition of such compounds, and a method of treatment of patients by administering an effective amount of a substituted 3-nitrobenzenesulfonamide to a patient in need of radiation therapy.

1 Claim, No Drawings

SUBSTITUTED 3-NITROBENZENESULFONAMIDES USEFUL AS ADJUNCTS IN RADIATION THERAPY

BACKGROUND OF THE INVENTION

This invention relates to novel substituted 3-nitrobenzensulfonamides compounds used as sensitizers of hypoxic tumor cells to therapeutic radiation. It also relates to a method of enhancing the therapeutic effect of radiation which comprises administering to a patient in need of such radiation treatment an effective amount of a substituted 3-nitrobenzensulfonamide and to pharmaceutical compositions containing a therapeutically effective amount of said substituted 3-nitrobenzensulfonamide.

At the present time, certain other unrelated compounds are in experimental clinical use as radiation sensitizers. However, these compounds—for example, metronidazole and misonidazole—suffer from the drawback that they also cause neurotoxicity which limits their usefulness. The compounds useful in the present invention are effective radiation sensitizers and are believed to have a more favorable therapeutic ratio.

DETAILED DESCRIPTION OF THE INVENTION

The compounds useful in the preparation of the pharmaceutical compositions of our invention are substituted 3-nitrobenzensulfonamides, or physiologically acceptable salts thereof, of the formula:

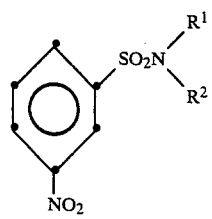
I wherein $R^1$ and $R^2$ are the same or different and are each separately hydrogen, lower alkyl of from 1-4 carbon atoms, hydroxyloweralkyl, tris (hydroxymethyl)-methyl, allyl, amino-(lower alkyl), (lower alkyl)-amino (lower alkyl), di(lower alkyl)-amino-(lower alkyl), azacycloalkyl)loweralkyl) or when taken together along with the nitrogen to which they are attached represent an heterocyclic ring selected from morpholino- or $R^4$-substituted 3-oxo-piperazinl-yl

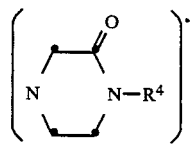

wherein $R^4$ is hydrogen, lower alkyl of from 1-4 carbon atoms or hydroxyalkyl of from 1-4 carbon atoms, with the proviso that $R^1$ and $R^2$ are not both hydroxyloweralkyl.

The substituted 3-nitrobenzensulfonamides of the present invention are prepared in the following manner.

A mixture of 3-nitrobenzenesulfonylchloride in an aprotic solvent such as tetrahydrofuran, dioxane, dimethyoxyethane, or chloroform is treated with at least an equimolar amount of an amine of the formula:

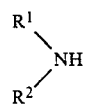
II wherein $R^1$ is $R^2$ are defined as set forth hereinabove.

It is preferred to carry out the reaction in the presence of a base in sufficient amount to neutralize the hydrogen chloride formed in the course of the reaction. The base used may be a tertiary amine such as triethylamine or pyridine. On the other hand, the same results may be produced by adding at least twice the molar amount of the reactant amine theoretically required. In this event, the reactant amine is utilized both to form the sulfonamide and to neutralize the hydrogen chloride formed in the amination reaction.

The temperature at which the reaction is carried out is not critical and may vary from 0°-100° C. or at the reflux temperature of the solvent, if under 100° C. The reaction temperature is preferably maintained at about 0°-25° C. for a period of 1-24 hours. The amination reaction may be formulated as follows:

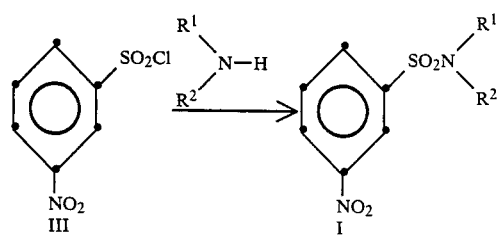

wherein $R^1$ and $R^2$ are as defined hereinabove.

In accordance with one embodiment of the present invention there is provided a novel substituted 3-nitrobenzenesulfonamide, or physiologically acceptable salts thereof, of the formula:

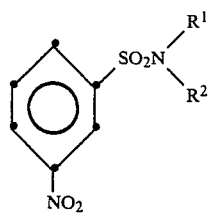
IV wherein $R^1$ and $R^2$ are the same or different and are each separately selected from hydrogen, lower alkyl of from 1-4 carbon atoms, hydroxy (lower alkyl) tris(hydroxymethyl)methyl, allyl, amino-(lower alkyl), (lower alkyl)-amino-(lower alkyl), di(-lower alkyl)-amino(-lower alkyl), azacycloalkyl(lower alkyl) or when taken together along with the nitrogen to which they are attached represent an heterocyclic ring selected from morpholino or $R^4$-substituted 3-oxo-piperazin-l-yl-

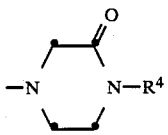

wherein $R^4$ is hydrogen, lower alkyl of from 1-4 carbon atoms, or hydroxyalkyl of from 1-4 carbon atoms, with the proviso that $R^1$ and $R^2$ are not both hydroxy(lower alkyl).

In accordance with a further embodiment of our invention, there are provided pharmaceutical formulations for the treatment of human patients or domestic animals undergoing radiation treatment of malignant disease processes comprising an effective amount of a radiation sensitizing compound of the formula:

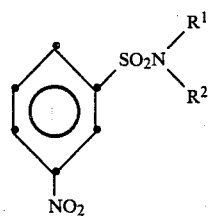

I and a pharmaceutically acceptable non-toxic carrier. The dosage form for intravenous administration is a sterile isotonic solution of the radiation sensitizing compound. Oral dosage forms such as tablets, capsules or elixirs may also be used.

Capsules or tablets containing 25, 50 100 or 500 mg of drug/capsule or tablet are satisfactory for use in the method of treatment of our invention.

In accordance with a still further embodiment of our invention, there is provided a method of treatment of human patients or domestic animals which comprises administering to a patient undergoing radiation treatment of malignant disease processes, an effective amount of a radiation sensitizing composition comprising a compound of the formula:

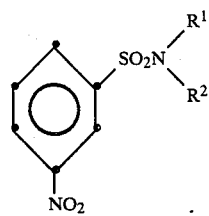

where $R_1$ and $R^2$ are as defined hereinabove. This method of treatment of affected individuals undergoing radiation treatment of malignant disease processes employs the compounds of the present invention in pharmaceutical compositions that are administered orally or intravenously. The dose employed depends on the radiation protocol for each individual patient. In protocols where the radiation dose is divided into a large number of fractions, the drug can be administered at intervals in the schedule and not necessarily with each radiation treatment. It should be noted that the compounds of the present invention are not intended for chronic administration. In general, the drug is administered from 10 minutes to 5 hours prior to the radiation treatment in a dosage amount of between 0.25 to about 4.0 grams per square meter of body surface.

The dosage range given is the effective dosage range and the decision as to exact dosage used must be made by the administering physician based on his judgment of the patient's general physical condition. In determining the dose for an individual patient, the physician may begin with an initial dose of 0.25 g/square metre of body surface to determine how well the drug is tolerated and increase the dose with each succeeding radiation treatment observing the patient carefully for any drug side-effect. The composition to be administered is an effective amount of the active compound and a pharmaceutical carrier for said active compound.

The following is a description of the method of preparation of specific active compounds and is intended to illustrate but not limit the process of preparation, product, composition, or method of treatment aspects of the invention. Temperatures are in degrees Celsius unless otherwise indicated throughout the application.

EXAMPLE 1

N,N-Di(2-hydroxyethyl)-3-nitrobenzenesulfonamide

A solution of diethanolamine (2.1 g, 20 mmol) in tetrahydrofuran (20 ml) was added slowly to a stirred solution of 3-nitrobenzenesulfonyl chloride (2.2 g, 10 mmol) in tetrahydrofuran (80 ml) at 20°-25°. After stirring at this temperature for 3 days, solvent was removed under reduced pressure. The residue was partitioned between ethyl acetate and water. After drying the ethyl acetate extract ($Na_2SO_4$), filtering and concentrating, the residue was recrystallized from ethyl acetate-hexane to give 0.89 g of the sulfonamide, m.p. 100°-102° C.

EXAMPLE 2

N-(2-Dimethylaminoethyl)-3-nitrobenzenesulfonamide hydrochloride

A solution of 2-dimethylaminoethylamine (2.2 ml, 20 mmol) in tetrahydrofuran (25 ml) was added over 30 minutes to a stirred solution of 3-nitrobenzenesulfonyl chloride (2.2 g, 10 mmol) in tetrahydrofuran (50 ml) cooled in an ice bath. After addition was complete, the reaction mixture was stirred in the ice bath for 30 minutes, then at 20°-25° for 20 hours. Solvent was removed under reduced pressure and the residue partitioned between ethyl acetate and water. The ethyl acetate extract was washed with a saturated aqueous solution of sodium chloride, dried ($Na_2SO_4$), filtered and concentrated. The residue was flash chromatographed on silica gel and eluted with 5% methanol-95% chloroform to give pure base. Further purification was effected by conversion to the HCl salt (1.75 g), m.p. 174.0°-76.0° C.

EXAMPLE 3

N-(1,3-Dihydroxy-2-hydroxymethyl-2-propyl)3-nitrobenzenesulfonamide

A mixture of 3-nitrobenzenesulfonyl chloride (2.5 g, 11.3 mmol), 2-amino-2-hydroxymethyl-1,3-propanediol (2.75 g, 22.7 mmol) in tetrahydrofuran (50 ml) and diemthylformamide (75 ml) was heated at 50° for 4 hours. Sovlents were removed under reduced pressure and the residue extracted with warm ethyl acetate. After filtering and concentrating the ethyl acetate extract, the residue was flash chromatographed over silica gel and product eluted with 5% methanol-95% chloroform. An analytical sample, m.p. 98°-9°, was obtained upon recrystallization from ethyl acetate-hexane.

What is claimed is:

1. N-(1,3-dihydroxy-2-hydroxymethyl-2-propyl)-3-nitrobenzenesulfonamide, or physiologically acceptable salt thereof.

* * * * *